(12) United States Patent
Hosokawa et al.

(10) Patent No.: US 6,515,182 B2
(45) Date of Patent: Feb. 4, 2003

(54) ARYLAMINE COMPOUND AND ORGANIC ELECTROLUMINESCENCE DEVICE

(75) Inventors: Chishio Hosokawa, Chiba (JP); Masakazu Funahashi, Chiba (JP)

(73) Assignee: Idemitsu Kosan Co., Ltd. (JP)

( * ) Notice: Subject to any disclaimer, the term of this patent is extended or adjusted under 35 U.S.C. 154(b) by 0 days.

(21) Appl. No.: 09/945,633

(22) Filed: Sep. 5, 2001

(65) Prior Publication Data

US 2002/0137969 A1 Sep. 26, 2002

(30) Foreign Application Priority Data

Sep. 5, 2000 (JP) ........................................ 2000-268833

(51) Int. Cl.⁷ ............................................. C07C 211/00
(52) U.S. Cl. ..................... 564/427; 564/307; 564/308; 428/690; 428/917; 313/504; 313/506
(58) Field of Search ................................. 564/307, 308, 564/427; 428/690, 917; 313/506, 504

(56) References Cited

U.S. PATENT DOCUMENTS 5,804,322 A * 9/1998 Shi et al.
5,985,417 A * 11/1999 Shi et al.

FOREIGN PATENT DOCUMENTS

| EP | 0 823 669 A1 | 8/1997 |
|---|---|---|
| EP | 0 879 868 A2 | 5/1998 |
| JP | 04181260 A | 6/1992 |
| JP | 04186362 A | 7/1992 |
| JP | 07297408 A | 10/1995 |
| JP | 11167992 A | 6/1999 |
| JP | 11184119 A | 7/1999 |

* cited by examiner

*Primary Examiner*—Samuel Barts
(74) *Attorney, Agent, or Firm*—Parkhurst & Wendel, L.L.P.

(57) ABSTRACT

A novel arylamine compound represented by the following general formula (1):

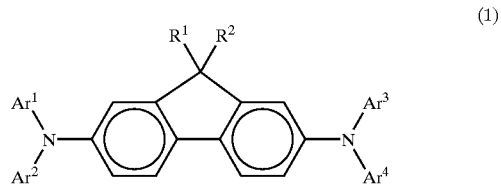

wherein $R^1$ and $R^2$ each independently represent an alkyl group, an alkoxyl group, an aryl group, an arylalkyl group or an aryloxyl group, $Ar^1$ to $Ar^4$ each independently represent an aryl group or a heterocyclic group, with provisos that at least two of $Ar^1$ to $Ar^4$ each represent m-biphenyl group or a biphenyl group substituted with aryl groups and the others of $Ar^1$ to $Ar^4$ each represent biphenyl group and that, when the biphenyl group substituted with aryl groups is a biphenyl group substituted with two aryl groups, the others of $Ar^1$ to $Ar^4$ each represent an aryl group; and an organic electroluminescence device comprising a layer of organic compounds which comprises the novel arylamine compound. The organic electroluminescence device has a high luminance, excellent heat resistance and a long life and emits light at a high efficiency. The novel arylamine compound provides the advantageous properties to the organic electroluminescence device.

5 Claims, No Drawings

ARYLAMINE COMPOUND AND ORGANIC ELECTROLUMINESCENCE DEVICE

TECHNICAL FIELD

The present invention relates to a novel arylamine compound and an organic electroluminescence device and, more particularly, to an organic electroluminescence device having a high luminance, excellent heat resistance, a long life and an excellent hole transporting property and emits light at a high efficiency and a novel arylamine compound providing the advantageous properties to the organic electroluminescence device.

BACKGROUND ART

Organic electroluminescence (referred to as EL, hereinafter) devices are used for a planar light emitting member such as a flat panel display of wall televisions and a back light of displays and the development of EL devices has been widely conducted.

Light emission from an organic substance under an electric field was observed in 1963 by Pope as light emission from a single crystal of anthracene (J. Chem. Phys., 38 (1963) 2042). In 1965, Helfinch and Schneider succeeded in observing relatively strong electroluminescence of the injection type using a solution electrode system having a good efficiency of injection (Phys. Rev. Lett., 14 (1965) 229). Since then, studies on forming organic light emitting substances from conjugated organic host substances and conjugated organic activating agents having condensed benzene rings have been reported. As the examples of the organic host substance, naphthalene, anthracene, phenanthrene, tetracene, pyrene, benzopyrene, chrysene, picene, carbazole, fluorene, biphenyl, terphenyl, triphenylene oxide, dihalobiphenyls, trans-stilbene and 1,4-diphenylbutadiene were shown. As the examples of the activating agent, anthracene, tetracene and pentacene were shown. However, these organic light emitting substances existed as a single layer having a thickness exceeding 1 μm and a high electric field was required for the light emission. Therefore, studies on a thin layer device using the vacuum vapor deposition process have been conducted (for example, Thin Solid Films, 94 (1982) 171). However, a device exhibiting a sufficiently high luminance for practical application could not be obtained although the use of the thin layer was effective for decreasing the driving voltage.

Tang et al. prepared an EL device having two very thin films (a hole transporting layer and a light emitting layer) which were laminated in accordance with the vacuum vapor deposition process and disposed between the anode and the cathode and succeeded in obtaining a high luminance under a low driving voltage (Appl. Phys. Lett., 51 (1987) 913 and U.S. Pat. No. 4,356,429). Thereafter, the development of organic compounds used for the hole transporting layer and the light emitting layer was conducted for more than a dozen years and the life and the efficiency of light emission sufficient for practical application could be achieved. As the result, the practical application of the organic EL device started in the area of displays of automobile stereos and portable telephones.

However, the luminance of light emission and the durability against degradation after the use for a long time are not sufficient for practical applications and further improvements are required. In particular, when an organic El device is applied to full color displays, it is required that the luminance be as high as 300 cd/m$^2$ or greater and a half-life be as long as several thousand hours or longer with respect to each of R, G and B colors. It is particularly difficult that these properties are achieved with respect to blue light. For the emission of blue light, the gap of the light emitting layer must be as great as 2.8 eV or greater. The energy barrier in the hole injection between the hole transporting layer and the light emitting layer is great and the intensity of the electric field applied to the interface is great. Therefore, stable hole injection cannot be achieved by using a conventional hole transporting layer and the improvement has been desired.

When application of an organic EL device to automobiles is considered, conventional organic EL devices have a problem in storage at a high temperature such as a temperature of 100° C. or higher. Conventional hole transporting layers have low glass transition temperatures and it was found that overcoming this problem by simply raising the glass transition temperature to a temperature exceeding 100° C. was not unsuccessful. Thus, the sufficient property for storage at high temperatures has not been achieved. Moreover, a problem arises in that exciplexes are formed by the interaction between the hole transporting layer and the light emitting layer and the luminance of the device deteriorates.

DISCLOSURE OF THE INVENTION

The present invention has been made to overcome the above problems and has an object of providing an organic EL device having a high luminance, excellent heat resistance, a long life and an excellent hole transporting property and emits light at a high efficiency and a novel arylamine compound providing the advantageous properties to the organic electroluminescence device.

As the result of extensive studies by the present inventors to develop an organic EL device having the above advantageous properties, it was found that, when a novel arylamine compound having a specific structure is added to the layer of organic compounds, the luminance, the heat resistance, the life and the hole transporting property of the organic EL device are improved and a high efficiency of light emission can be achieved. The present invention has been completed based on the knowledge.

The present invention provides:

A novel arylamine compound represented by the following general formula (1):

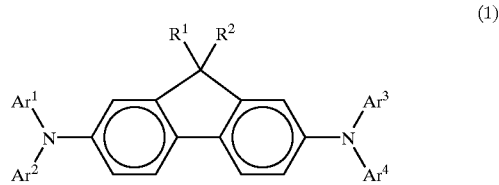

(1)

wherein R$^1$ and R$^2$ each independently represent a substituted or unsubstituted alkyl group having 1 to 30 carbon atoms, a substituted or unsubstituted alkoxyl group having 1 to 30 carbon atoms, a substituted or unsubstituted aryl group having 6 to 40 carbon atoms, a substituted or unsubstituted arylalkyl group having 7 to 40 carbon atoms or a substituted or unsubstituted aryloxyl group having 6 to 40 carbon atom; and Ar$^1$ to Ar$^4$ each independently represent a substituted or unsubstituted aryl group having 6 to 40 carbon atoms or a substituted or unsubstituted heterocyclic group having 5 to 40 carbon atoms and may represent a same group or different groups, with provisos that at least two of $Ar^1$ to $Ar^4$ each represent a substituted or unsubstituted m-biphenyl group or biphenyl group substituted with aryl groups and others of $Ar^1$ to $Ar^4$ each represent a substituted or unsubstituted biphenyl group and that, when at least two of $Ar^1$ to $Ar^4$ each represent biphenyl group substituted with two aryl groups, others of $Ar^1$ to $Ar^4$ each represent a substituted or unsubstituted aryl group; and A novel arylamine compound represented by the following general formula (2):

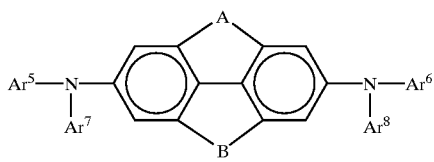

(2)

wherein at least one of A and B represents an atom group forming a substituted or unsubstituted saturated five-membered to eight-membered ring which may comprise a spiro bond, with provisos that, when any one of A and B represents an atom group forming a saturated five-membered ring, A and B each represent a group forming a ring structure or any of A and B represents a group comprising a spiro bond and that at least one of A and B represents a group which does not comprise two or more unsaturated six-membered rings; and $Ar^5$ to $Ar^8$ each independently represent a substituted or unsubstituted aryl group having 6 to 40 carbon atoms or a substituted or unsubstituted heterocyclic group having 5 to 40 carbon atoms and may represent a same group or different groups.

The present invention further provides an electroluminescence device comprising a pair of electrodes and a layer of organic compounds disposed between the pair of electrodes, wherein the layer of organic compounds comprises the novel arylamine compound described above.

THE MOST PREFERRED EMBODIMENT TO CARRY OUT THE INVENTION

The novel arylamine compound of the present invention is represented by general formula (1) or general formula (2) shown above.

In general formula (1), $R^1$ and $R^2$ each independently represent a substituted or unsubstituted alkyl group having 1 to 30 carbon atoms, a substituted or unsubstituted alkoxyl group having 1 to 30 carbon atoms, a substituted or unsubstituted aryl group having 6 to 40 carbon atoms, a substituted or unsubstituted arylalkyl group having 7 to 40 carbon atoms or a substituted or unsubstituted aryloxyl group having 6 to 40 carbon atom.

Examples of the alkyl group include methyl group, ethyl group, n-propyl group and isopropyl group. Examples of the alkoxyl group include methoxyl group and ethoxyl group. Examples of the aryl group include phenyl group, biphenyl group and naphthyl group. Examples of the arylalkyl group include benzyl group, α-methylbenzyl group, α-ethylbenzyl group, α,α-dimethylbenzyl group, 4-methylbenzyl group, 4-ethylbenzyl group, 2-tert-butylbenzyl group, 4-n-octylbenzyl group, naphthylmethyl group and diphenylmethyl group. Examples of the aryloxyl group include phenoxyl group, naphthyloxyl group, anthryloxyl group, pyrenyloxyl group, fluoranthenyloxyl group, chrysenyloxyl group and perylenyloxyl group.

Examples of the substituent to the above groups include halogen atoms such as fluorine atom, chlorine atom, bromine atom and iodine atom; alkyl groups such as methyl group, ethyl group, n-propyl group and isopropyl group; alkoxyl groups such as methoxyl group and ethoxyl group; aryloxyl groups such as phenoxyl group; arylalkyl groups such as benzyl group, phenetyl group and phenylpropyl group; nitro group; cyano group; substituted amino groups such as dimethylamino group, dibenzylamino group, diphenylamino group and morpholino group; aryl groups such as phenyl group, tolyl group, biphenyl group, naphthyl group, anthryl group and pyrenyl group; and heterocyclic groups such as pyridyl group, thienyl group, furyl group, quinolyl group and carbazolyl group.

In general formula (1), $Ar^1$ to $Ar^4$ each independently represent a substituted or unsubstituted aryl group having 6 to 40 carbon atoms or a substituted or unsubstituted heterocyclic group having 5 to 40 carbon atoms and may represent the same group or different groups.

Examples of the aryl group include aryl groups such as phenyl group, tolyl group, biphenyl group, naphthyl group, anthryl group and pyrenyl group. Examples of the heterocyclic group include pyridyl group, thienyl group, furyl group, quinolyl group and carbazolyl group.

In general formula (1), at least two of $Ar^1$ to $Ar^4$ each represent a substituted or unsubstituted m-biphenyl group or biphenyl group substituted with aryl groups and the others of $Ar^1$ to $Ar^4$ each represent a substituted or unsubstituted biphenyl group. However, when at least two of $Ar^1$ to $Ar^4$ each represent biphenyl group substituted with two aryl groups, the others of $Ar^1$ to $Ar^4$ each represent a substituted or unsubstituted aryl group.

Examples of the substituent to the groups represented by $Ar^1$ to $Ar^4$ include halogen atoms such as fluorine atom, chlorine atom, bromine atom and iodine atom; alkyl groups such as methyl group, ethyl group, n-propyl group and isopropyl group; alkoxyl groups such as methoxyl group and ethoxyl group; aryloxyl groups such as phenoxyl group; arylalkyl groups such as benzyl group, phenetyl group and phenylpropyl group; nitro group; cyano group; substituted amino groups such as dimethylamino group, dibenzylamino group, diphenylamino group and morpholino group; aryl groups such as phenyl group, tolyl group, biphenyl group, naphthyl group, anthryl group and pyrenyl group; and heterocyclic groups such as pyridyl group, thienyl group, furyl group, quinolyl group and carbazolyl group.

Examples of the aryl group in the biphenyl group substituted with aryl groups include phenyl group, biphenyl group, terphenyl group, naphthyl group, anthryl group and fluorenyl group.

It is preferable that $Ar^1$ and $Ar^3$ each represent a substituted or unsubstituted m-biphenyl group and $Ar^2$ and $Ar^4$ each represent a substituted or unsubstituted biphenyl group.

In general formula (2), at least one of A and B represents an atom group forming a substituted or unsubstituted saturated five-membered to eight-membered ring which may comprise a spiro bond. When any one of A and B represents an atom group forming a saturated five-membered ring, A and B each represent a group forming a ring structure or any of A and B represents a group comprising a spiro bond. At least one of A and B represents a group which does not comprise two or more unsaturated six-membered rings.

The Spiro bond described above means a structure in which two saturated cyclic structures are bonded to each other through one atom, such as a carbon atom or silicon atom, which is a member of both cyclic structures. In the novel arylamine compound, it is preferable that the atom group represented by A or B comprises a spiro bond.

Examples of the atom forming the atom group represented by A or B include carbon atom and atoms other than carbon atom such as Si, O, S, N, B and P. These atoms may form a portion of the saturated cyclic structure. The saturated cyclic structure may have substituents such as alkyl groups, alkoxyl groups and aryl groups.

Examples of the biphenyl structure comprising the atom groups represented by at least one of A and B include the following structures:

(1-1)
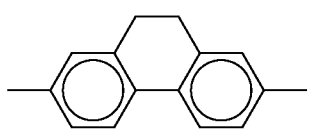

(1-2)
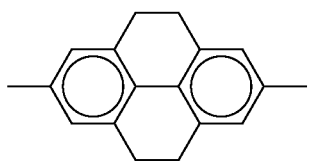

(1-3)
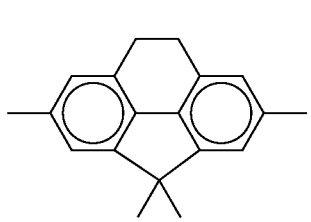

(1-4)
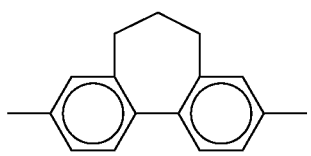

(1-5)
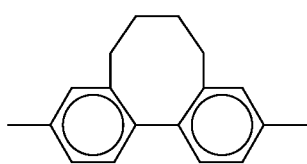

(1-6)
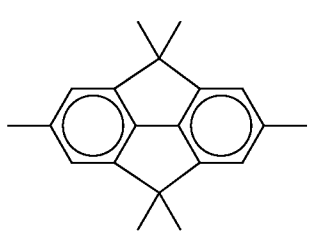

(1-7)
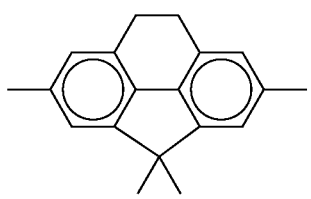

-continued (1-8)
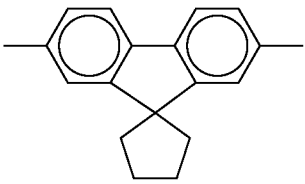

(1-9)
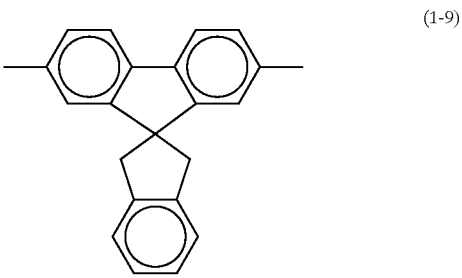

(1-10)
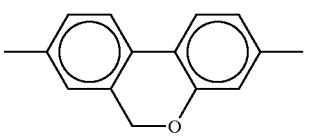

(1-11)
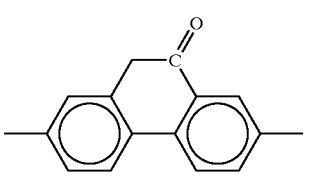

(1-12)
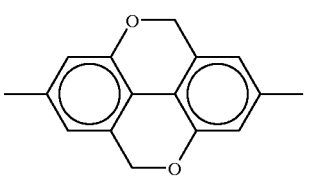

(1-13)
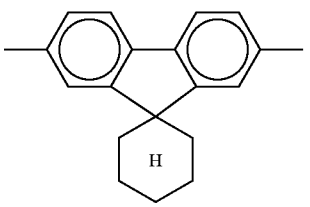

(1-14)
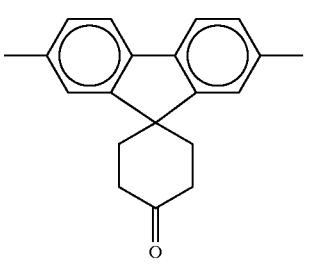

(1-15)
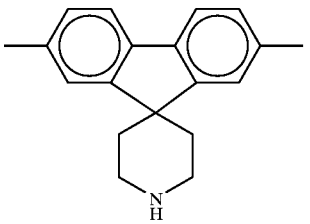

(1-16) 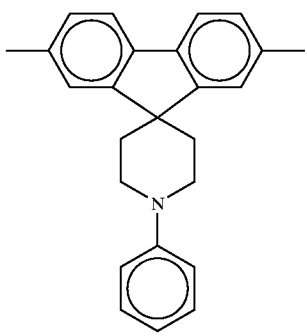

(1-17) 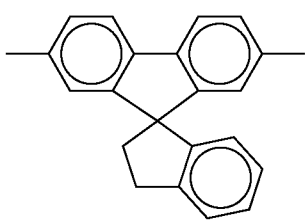

(1-18) 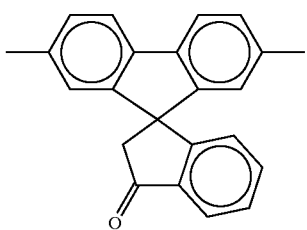

(1-19) 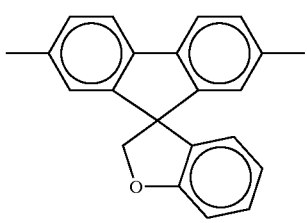

(1-20) 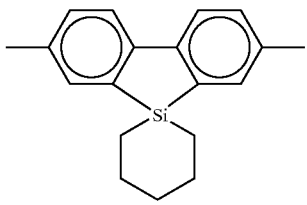

(1-21) 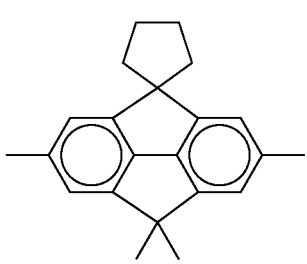

(1-22) 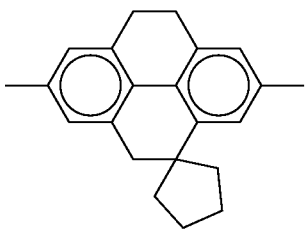

(1-23) 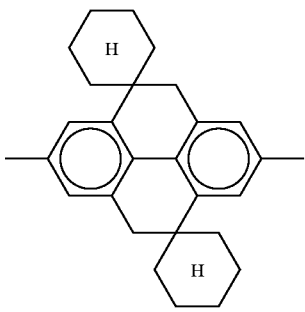

(1-24) 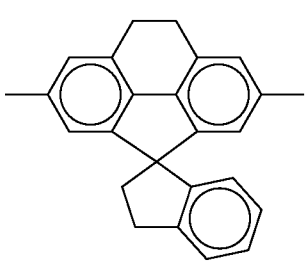

(1-25) 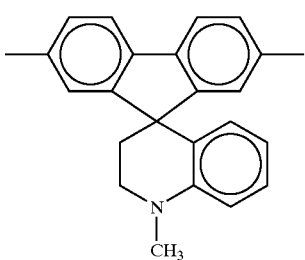

In general formula (2), $Ar^5$ to $Ar^8$ each independently represent a substituted or unsubstituted aryl group having 6 to 40 carbon atoms or a substituted or unsubstituted heterocyclic group having 5 to 40 carbon atoms and may represent the same group or different groups.

Examples of the substituted or unsubstituted aryl group include phenyl group, biphenyl group, terphenyl group, naphthyl group, anthryl group, fluorenyl group and fluoranthenyl group. Examples of the substituted or unsubstituted heterocyclic group include pyridyl group, furyl group, thienyl group and carbazolyl group.

Examples of the substituent to the above groups include halogen atoms such as fluorine atom, chlorine atom, bromine atom and iodine atom; alkyl groups such as methyl group, ethyl group, n-propyl group and isopropyl group; alkoxyl groups such as methoxyl group and ethoxyl group; aryloxyl groups such as phenoxyl group; arylalkyl groups such as benzyl group, phenetyl group and phenylpropyl group; nitro group; cyano group; substituted amino groups such as dimethylamino group, dibenzylamino group, diphenylamino group and morpholino group; aryl groups such as phenyl group, tolyl group, biphenyl group, naphthyl group, anthryl group and pyrenyl group; and heterocyclic groups such as pyridyl group, thienyl group, furyl group, quinolyl group and carbazolyl group.

In the novel arylamine compound represented by general formula (2), it is preferable that at least two of $Ar^5$ to $Ar^8$ each represent an aromatic hydrocarbon group having 12 or more carbon atoms. As the novel arylamine compound, it is more preferable that at least two of $Ar^5$ to $Ar^8$ each represent a substituted or unsubstituted biphenyl groups and at least one of $Ar^5$ to $Ar^8$ represents a group substituted with a diarylamino group.

The organic EL device of the present invention comprises a pair of electrodes and a layer of organic compounds disposed between the pair of electrodes and the layer of organic compounds comprises the novel arylamine compound described above.

It is preferable that the layer of organic compounds is a light emitting layer or a hole transporting layer. It is also preferable that the layer of organic compounds comprises a layer comprising the novel arylamine compound described above and a light emitting material.

The luminance, the heat resistance, the life and the efficiency of light emission of the organic EL device are improved by introducing the novel arylamine compound described above into at least one of the layers in the layer of organic compounds because the arylamine compound exhibits the excellent hole transporting property so that hole injection can be achieved with stability, has a high glass transition temperature and causes little interaction with the light emitting material so that the transition without radiation due to the interaction can be prevented.

Typical examples of the novel arylamine compound of the present invention represented by general formula (1) are shown as compounds (A-1) to (A-13) and typical examples of the novel arylamine compound of the present invention represented by general formula (2) are shown as compounds (B-1) to (B-20) in the following. However, the arylamine compound of the present invention is not limited to the compounds shown as the examples.

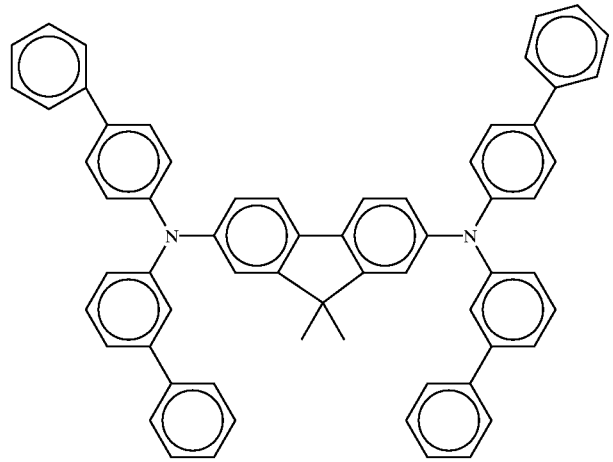

(A-1)

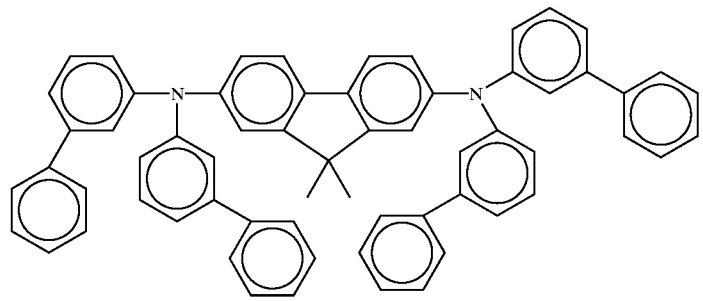

(A-2)

-continued
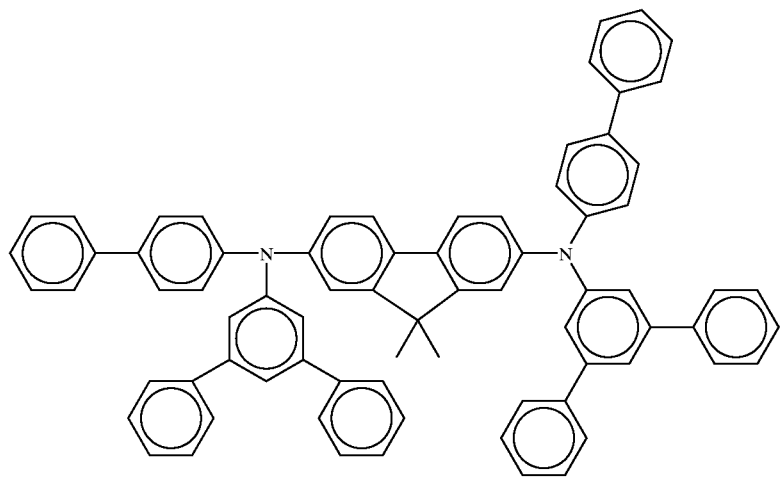
(A-3)
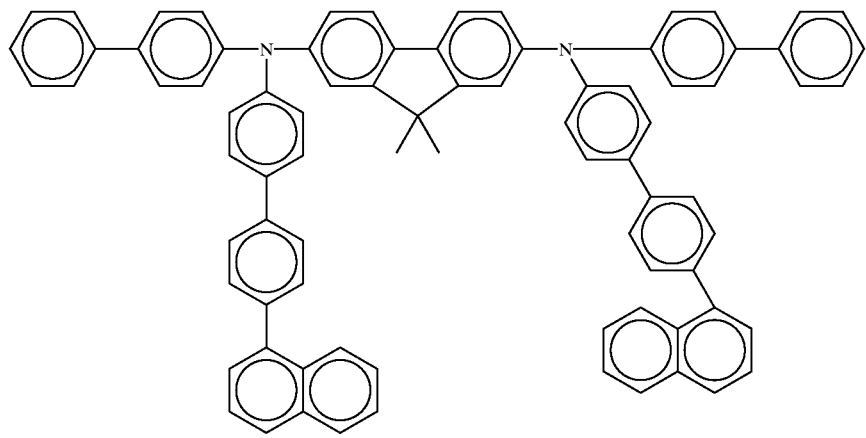
(A-4)
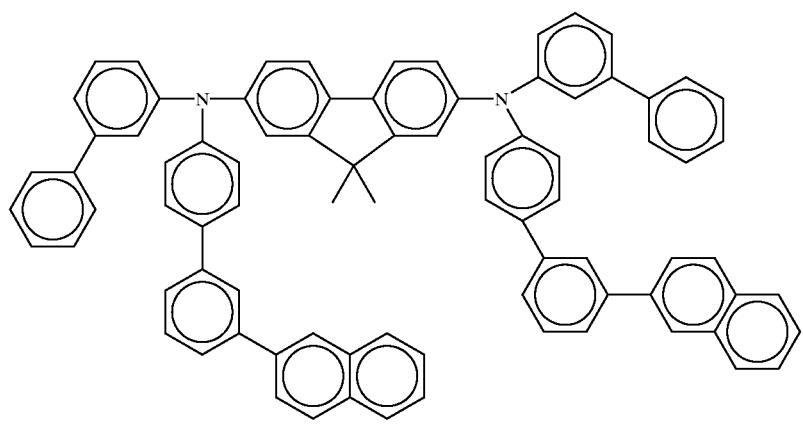
(A-5)

(A-6)
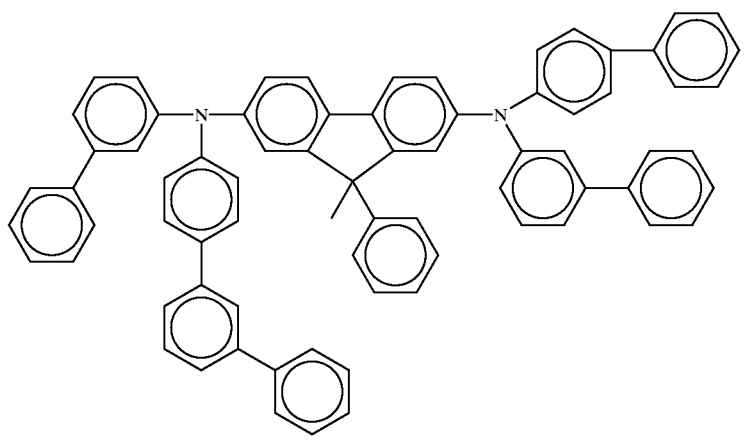
(A-7)
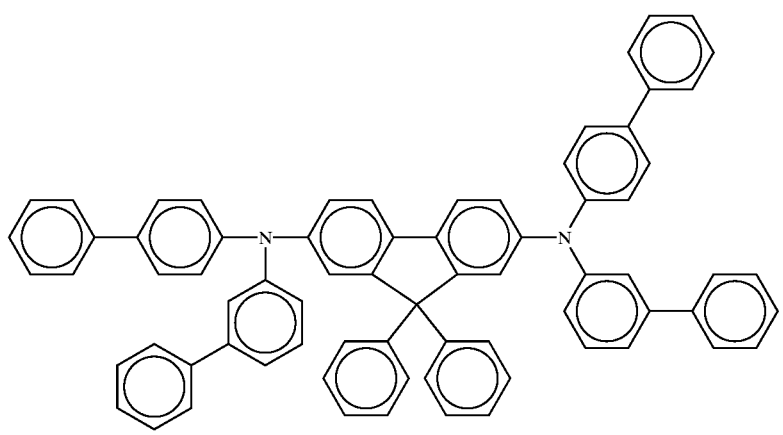
(A-8)
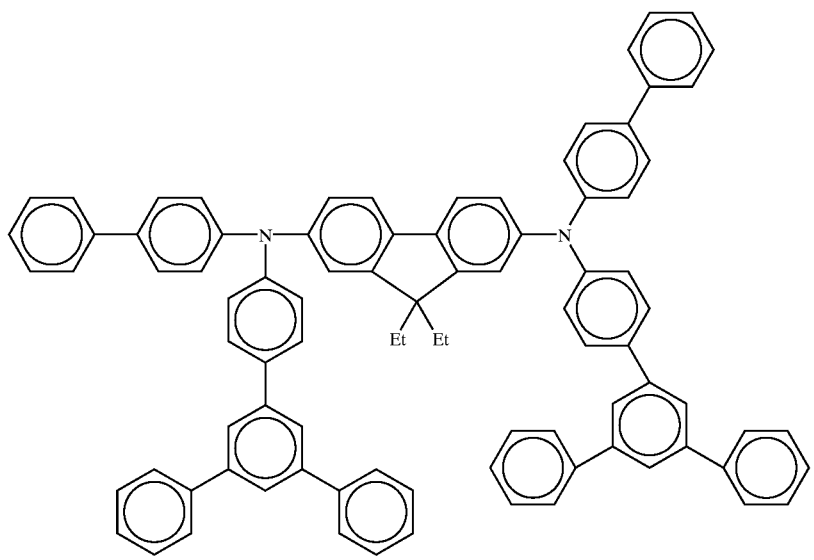

-continued
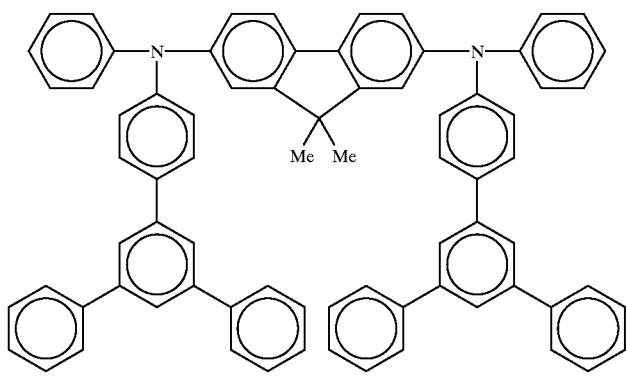
(A-9)
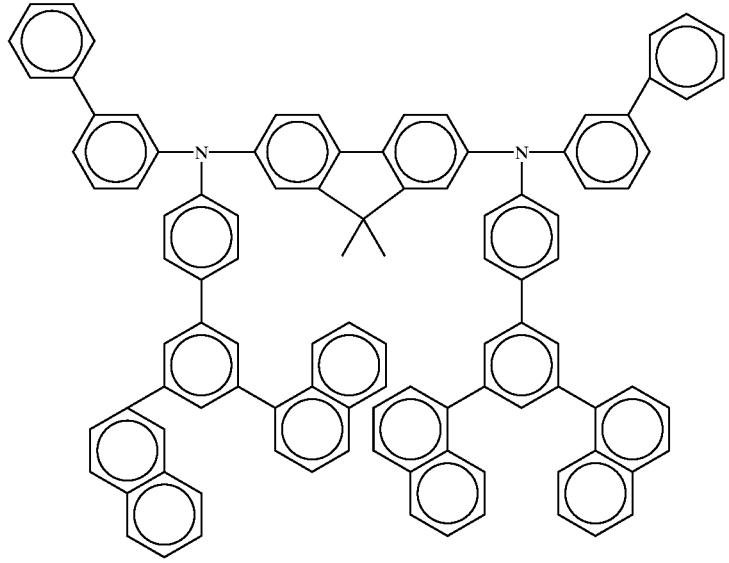
(A-10)
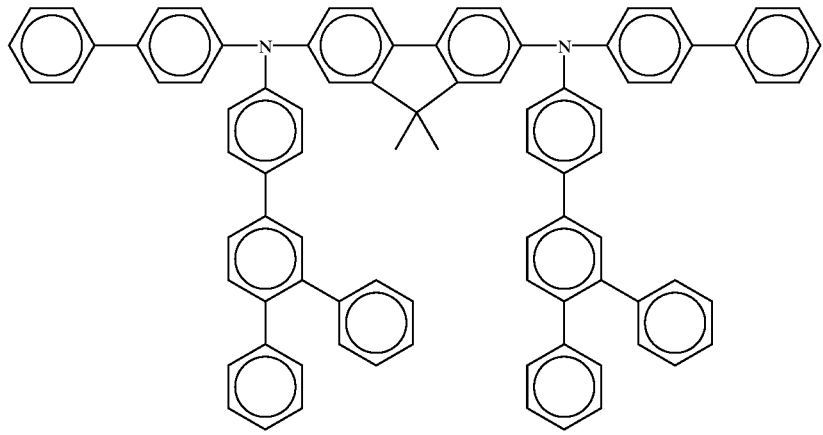
(A-11)
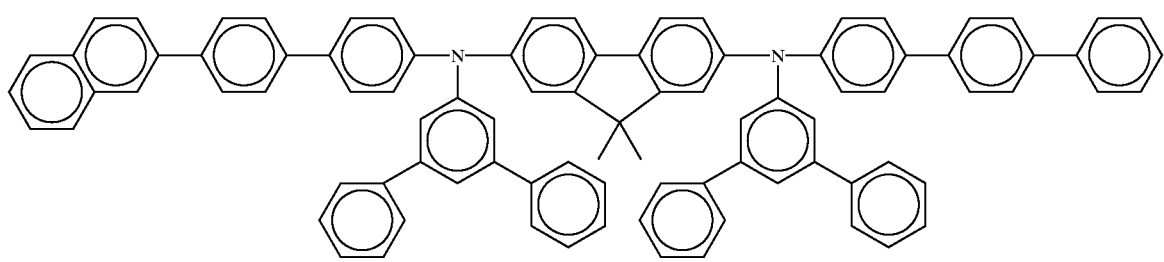
(A-12)

-continued
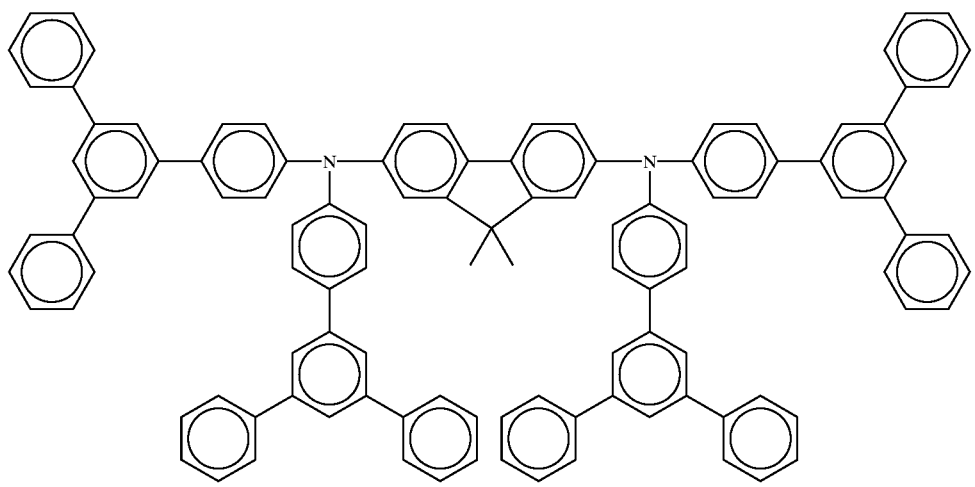
(A-13)
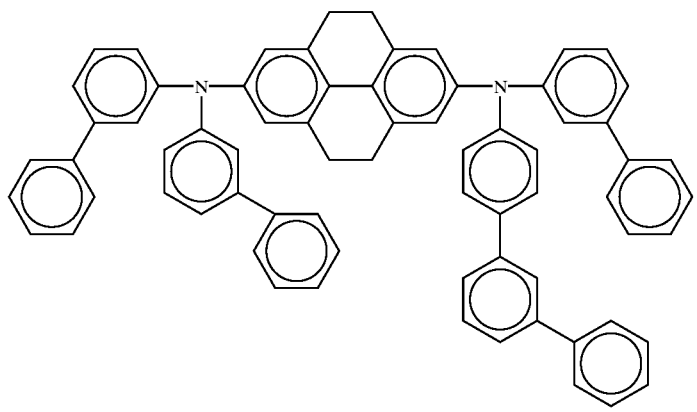
(B-1)
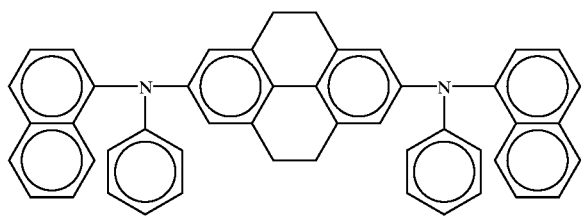
(B-2)
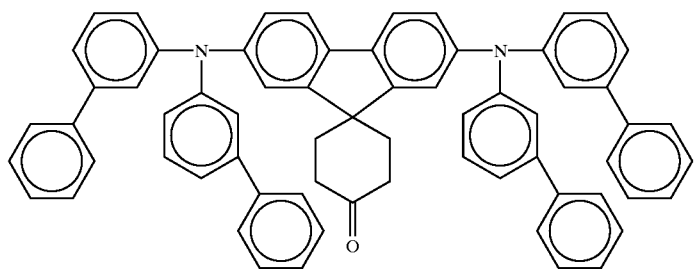
(B-3)

-continued
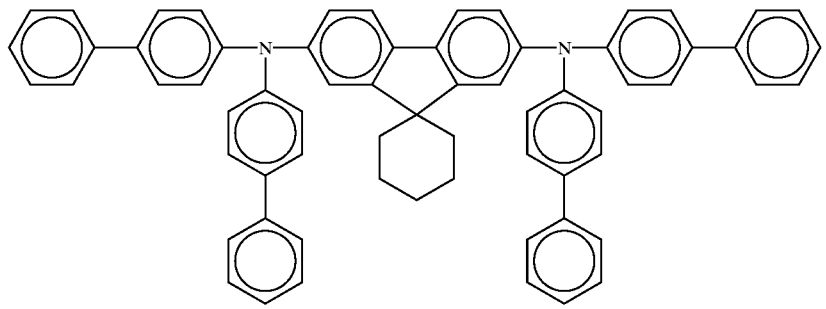
(B-4)
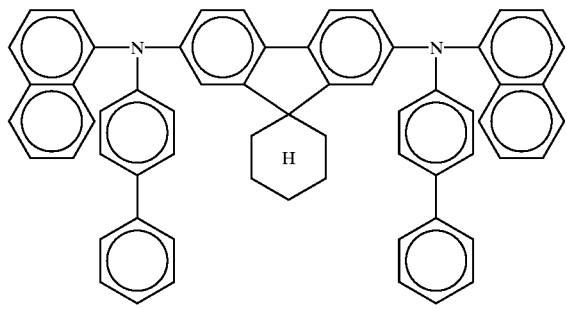
(B-5)
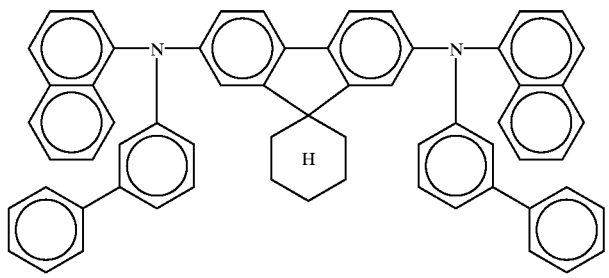
(B-6)
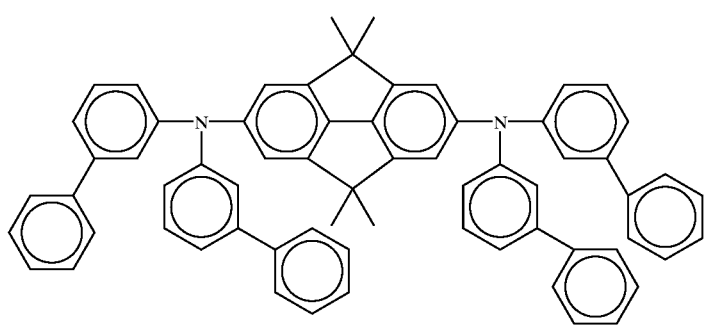
(B-7)
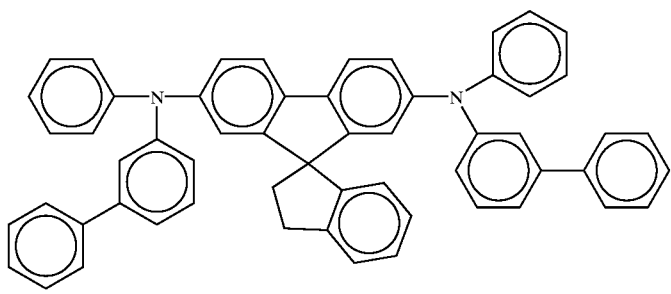
(B-8)

-continued
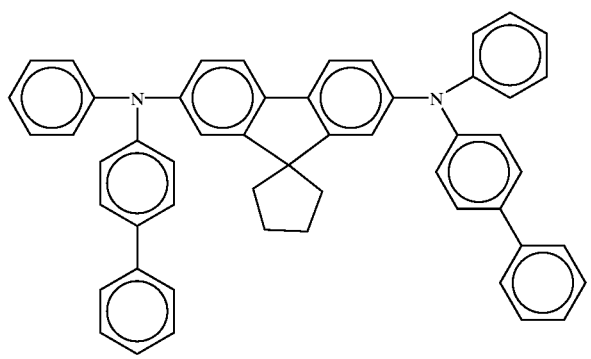
(B-9)
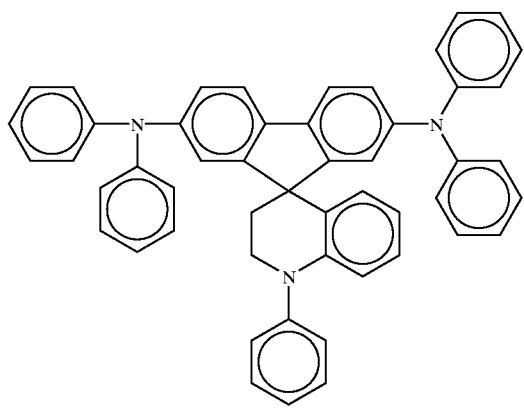
(B-10)
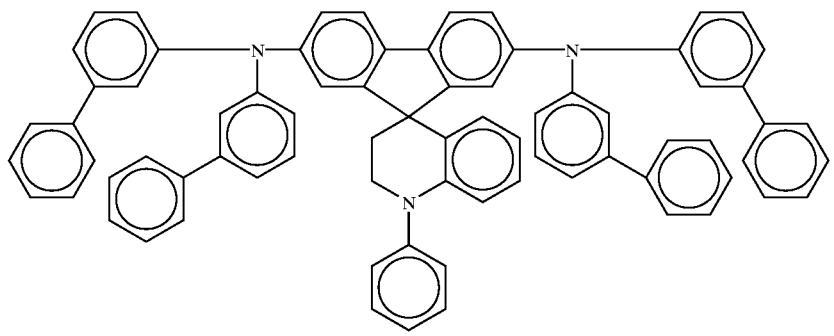
(B-11)
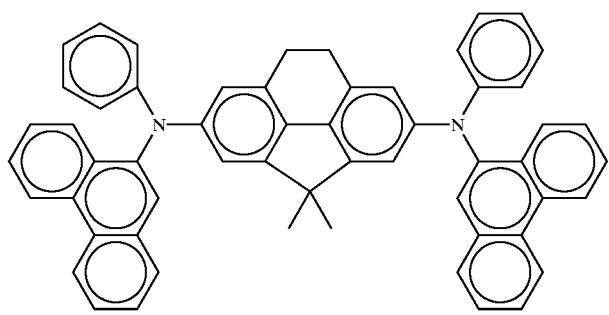
(B-12)

-continued
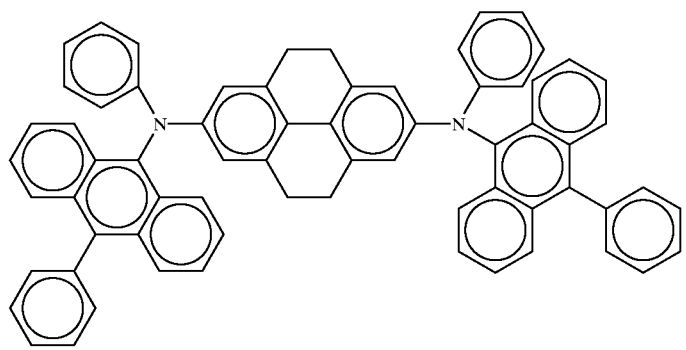
(B-13)
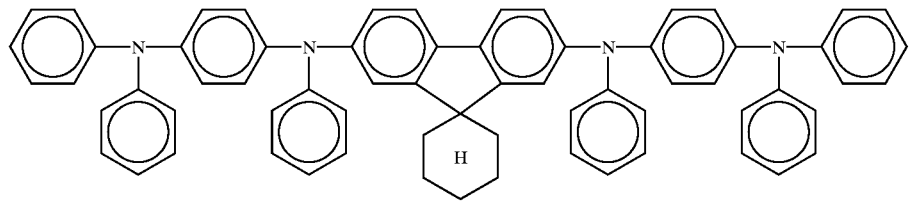
(B-14)
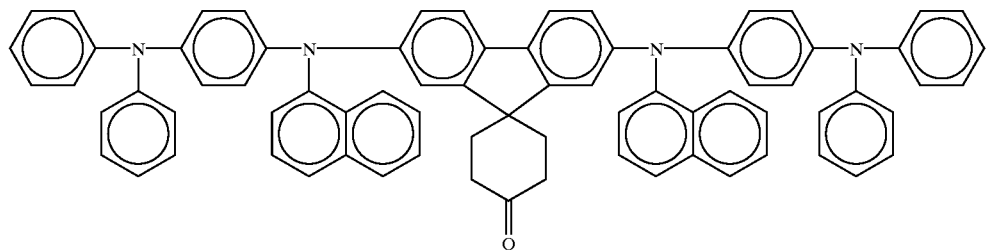
(B-15)
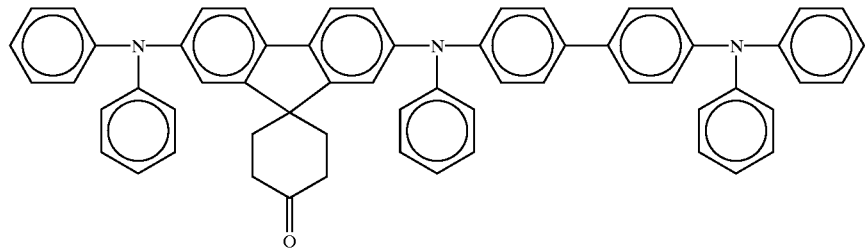
(B-16)
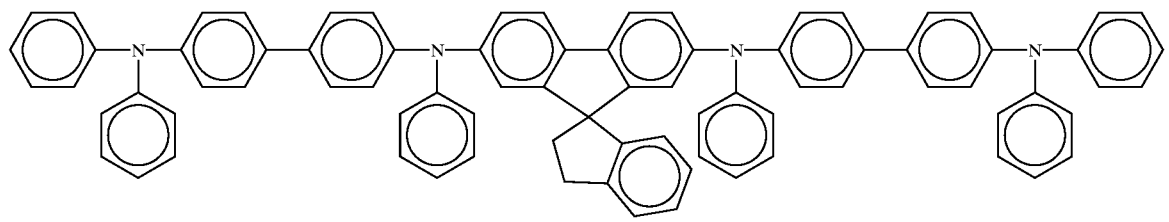
(B-17)
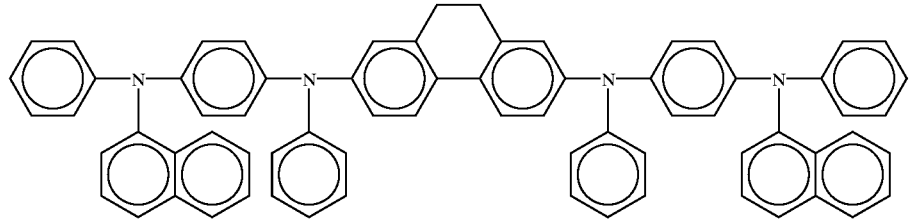
(B-18)

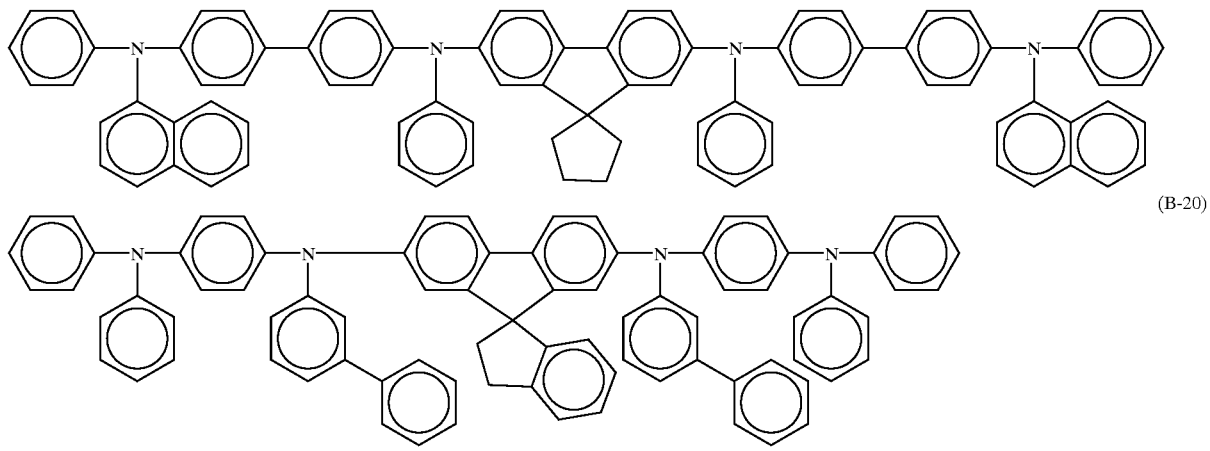

(B-19)

(B-20)

The organic EL device of the present invention is a device comprising a film of organic compounds having a single layer or a plurality of layers disposed between an anode and a cathode. When the film of organic compounds has a single layer, a light emitting layer is disposed between the anode and the cathode. The light emitting layer comprises a light emitting material and may further comprise a hole injecting material or an electron injecting material to transport holes injected from the anode or electrons injected from the cathode, respectively, to the light emitting material. However, it is preferable that the light emitting material has a very high fluorescent quantum efficiency and a combination of an excellent ability of transporting holes and an excellent ability of transporting electrons and can form a uniform thin film. When the film of organic compounds in the organic EL device has a plurality of layers, the organic EL device has a laminate structure of a plurality of layers such as (an anode/a hole injecting layer/a light emitting layer/a cathode), (an anode/a light emitting layer/an electron injecting layer/a cathode) and (an anode/a hole injecting layer/a light emitting layer/an electron injecting layer/a cathode).

In the light emitting layer, conventional light emitting materials, doping materials, hole injecting materials and electron injecting materials may further be used in addition to the novel arylamine compound of the present invention. It is preferable that the novel arylamine compound is introduced into a layer selected from the light emitting layer, the electron injecting layer, the hole transporting layer and the hole injecting layer in a concentration of 0.5 to 100% by weight. and more preferably in a concentration of 50 to 100% by weight.

By forming the organic EL device in a multi-layer structure, decreases in the luminance and the life due to quenching can be prevented. Where necessary, light emitting materials, doping materials, hole injecting materials and electron injecting materials may be used in combination. By using other doping materials, the luminance and the efficiency of the light emission can be improved and red light or white light can be emitted. The hole injecting layer, the light emitting layer and the electron injecting layer may be each formed in a laminate structure having two or more layers. When the hole injecting layer has a laminate structure having two or more layers, a layer into which holes are injected from the electrode is called the hole injecting layer and a layer which receives the holes from the hole injecting layer and transports the holes to the light emitting layer is called the hole transporting layer. Similarly, when the electron injecting layer has a laminate structure having two or more layers, a layer into which electrons are injected from the electrode is called the electron injecting layer and a layer which receives the electrons from the hole injecting layer and transports the electrons to the light emitting layer is called the electron transporting layer. The layer is selected and used in accordance with the properties of the material such as the energy level, heat resistance and adhesion with the film of organic compounds or the metal electrodes.

As the light emitting material or a host material which can be used for the film of organic compounds in combination with the novel arylamine compound, condensed polycyclic aromatic compounds can be used. Examples of the polycyclic aromatic compound include anthracene, naphthalene, phenanthrene, pyrene, tetracene, pentacene, coronene, chrysene, fluorescein, perylene, rubrene, phthaloperylene, naphthaloperylene, perynone, phthaloperynone, naphthaloperynone, diphenylbutadiene, tetraphenylbutadiene, coumarine, oxadiazole, aldazine, bisbenzoxazoline, bisstyryl, pyrazine, cyclopentadiene, metal complexes of quinoline, metal complexes of aminoquinoline, metal complexes of benzoquinoline, imines, diphenylethylene, vinylanthracene, diaminocarbazole, pyrane, thiopyrane, polymethine, merocyanine, oxinoid compounds chelated with imidazole, quinacridone, derivatives of stilbene and fluorescent coloring agents. However, the polycyclic aromatic compound is not limited to the above compounds described as the examples.

As the conventional hole injecting material, compounds having the ability of transporting holes, exhibiting the effect of injecting holes from the anode and the excellent effect of injecting holes to the light emitting layer or the light emitting material, preventing transfer of excited particles formed in the light emitting layer into the electron injecting layer or the electron injecting material and having the excellent ability of forming a thin film are preferable. Examples of the hole injecting material include phthalocyanine derivatives, naphthalocyanine derivatives, porphyrin derivatives, triazole, imidazole, imidazolone, imdazolethione, pyrazoline, pyrazolone, tetrahydroimidazole, oxazole, oxadiazole, hydrazone, acylhydrazone, polyarylalkanes, stilbene, butadiene, triphenylamines of the benzidine type, triphenylamines of the styrylamine type, triphenylamines of the diamine type, derivatives of the above compounds and macromolecular materials such as polyvinylcarbazole, polysilane and electrically conductive macromolecular compounds. However, the hole injecting material is not limited to the compounds described above as the examples.

Among the conventional hole injecting materials which can be used in the organic EL device of the present invention, aromatic tertiary amine derivatives and phthalocyanine derivatives are more effective.

Examples of the aromatic tertiary amine derivative include triphenylamine, tritolylamine, tolyldiphenylamine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4-diamine, N,N'-diphenyl-N,N'-dinaphthyl-1,1'-biphenyl-4,4'-diamine, N,N'-(methylphenyl)-N,N'-(4-n-butylphenyl)phenanthrene-9,10-diamine, N,N-bis(4-di-4-tolylaminophenyl)-4-phenylcyclohexane and oligomers and polymers having the skeleton structure of the aromatic tertiary amine described above. However, the aromatic tertiary amine derivative is not limited to the compounds described above as the examples.

Examples of the phthalocyanine (Pc) derivative include phthalocyanine derivatives and naphthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc and GaPc-O-GaPc. However, the phthalocyanine derivative is not limited to the compounds described above as the examples.

As the conventional electron injecting material, compounds having the ability of transporting electrons, exhibiting the effect of injecting electrons from the cathode and the excellent effect of injecting electrons into the light emitting layer or the light emitting material, preventing transfer of excited particles formed in the light emitting layer into the hole injecting layer and having the excellent ability of forming a thin film are preferable. Examples of the electron injecting material include fluorenone, anthraquinodimethane, diphenoquinone, thiopyrane dioxide, oxazole, oxadiazole, triazole, imidazole, perylenetetracarboxylic acid, fluorenylidenemethane, anthrone and derivatives of these compounds. However, the electron injecting material is not limited to the compounds described above as the examples. The charge injecting property can be improved by adding an electron accepting substance to the hole injecting material or an electron donating substance to the electron injecting material.

In the organic EL device of the present invention, metal complex compounds and five-membered ring derivatives containing nitrogen are more effective as the conventional electron injecting material.

Examples of the metal complex compound include 8-hydroxyquinolinatolithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum and bis(2-methyl-8-quinolinato)(2-naphtholato)gallium. However, the metal complex compound is not limited to the compounds described above as the examples.

As the five-membered ring derivative containing nitrogen, derivatives of oxazole, thiazole, oxadiazole, thiadiazole and triazole are preferable. Examples of such compounds include 2,5-bis(1-phenyl)-1,3,4-oxazole, dimethylPOPOP, 2,5-bis(1-phenyl)-1,3,4-thiazole, 2,5-bis(1-phenyl)-1,3,4-oxadiazole, 2-(4'-tert-butylphenyl)-5-(4"-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4"-biphenyl)-1,3,4-triazole, 2,5-bis(1-naphthyl)-1,3,4-triazole and 1,4-bis[2-(5-phenyltriazolyl)]benzene. However, the five-membered ring derivative containing nitrogen is not limited to the compounds described above as the examples.

In the present invention, a layer of an inorganic compound may be disposed between the light emitting layer and the electrode to improve the charge injecting property. As the inorganic compound used for the layer of an inorganic compound, alkali metal compounds such as fluorides and oxides of alkali metals and alkaline earth compounds can be used. Examples of the inorganic compound include LiF, $Li_2O$, RaO, SrO, $BaF_2$ and $SrF_2$.

As the electrically conductive material used for the anode of the organic EL device, materials having a work function greater than 4 eV are suitable. Examples of such materials include carbon, aluminum, vanadium, iron, cobalt, nickel, tungsten, silver, gold, platinum, palladium, alloys of. these metals, metal oxides used for ITO substrates and NESA substrates such as tin oxide and indium oxide and organic electrically conductive resins such as polythiophene and polypyrrole. As the electrically conductive material used for the cathode, materials having a work function smaller than 4 eV are suitable. Examples of such materials include magnesium, calcium, tin, lead, titanium, yttrium, lithium, ruthenium, manganese, aluminum and alloys of these materials. However, the materials for the electrodes are not limited to the materials described above as the examples. Examples of the alloy include magnesium/silver alloys, magnesium/indium alloys and lithium/aluminum alloys. However, the alloy is not limited to the alloys described above as the examples. The composition of the alloy is controlled by the temperature of the sources of vapor deposition, the atmosphere and the degree of vacuum and is selected suitably. The anode and the cathode may have a laminate structure having two or more layers, where necessary.

To obtain efficient light emission from the organic EL device, it is preferable that at least one face of the device is sufficiently transparent in the region of the wavelength of the light emitted by the device. It is preferable that the substrate is also transparent. The transparent electrode is prepared by using the above electrically conductive material in accordance with a suitable process such as the vapor deposition and the sputtering in a manner such that the specific transparency can be obtained. It is preferable that the electrode at the side of the light emitting face has a transmittance of the emitted light of 10% or greater. The substrate is not particularly limited as long as the substrate has a mechanical strength, shows strength at high temperatures and is transparent. Examples of the substrate include glass substrates and transparent films of resins. Examples of the transparent films include films of resins such as polyethylene, copolymers of ethylene and vinyl acetate, copolymers of ethylene and vinyl alcohol, polystyrene, polymethyl methacrylate, polyvinyl chloride, polyvinyl alcohol, polyvinyl butyral, nylon, polyether ether ketones, polysulfones, polyether sulfones, copolymers of tetrafluoroethylene and perfluoroalkyl vinyl ethers, polyvinyl fluoride, copolymers of tetrafluoroethylene and ethylene, copolymers of tetrafluoroethylene and hexafluoropropylene, polychlorotrifluoroethylene, polyvinylidene fluoride, polyesters, polycarbonates, polyurethanes, polyether imides, polyimides and polypropylene.

To improve the stability of the organic EL of the present invention to heat, moisture and the atmosphere, a protective layer may be formed on the surface of the device or the entire device may be coated with a silicone oil or a resin for protection.

For forming the layers in the organic EL device, any process can be selected from dry processes for film formation such as the vacuum vapor deposition process, the sputtering process, the plasma process and the ion plating process and wet processes for film formation such as the spin coating process, the dipping process and the flow coating process. The thickness of the film is not particularly limited. It is necessary that the thickness of the film be set within a suitable range. When the thickness of the film is greater than the suitable range, it is necessary that a great voltage be applied to obtain a specific output of the light and the efficiency decreases. When the thickness of the film is smaller than the suitable range, pin holes are formed and a sufficient luminance cannot be obtained when an electric field is applied. In general, it is preferable that the thickness of the film is in the range of 5 nm to 10 $\mu$m and more preferably in the range of 10 nm to 0.2 $\mu$m.

When a wet process for the film formation is used, the material for forming each layer is used for forming the thin film after the material is dissolved or dispersed in a suitable solvent such as ethanol, chloroform, tetrahydrofuran and dioxane. As the solvent, any of the above solvents can be used. In any of the layers of the organic thin films, suitable resins or additives may be used for improving the properties of the films and preventing formation of pin holes. Examples of the resin which can be used include insulating resins such as polystyrene, polycarbonates, polyarylates, polyesters, polyamides, polyurethanes, polysulfones, polymethyl methacrylate, polymethyl acrylate, cellulose and copolymers of these resins; photoconductive resins such as poly-N-vinylcarbazole and polysilane; and electrically conductive resins such as polythiophene and polypyrrole. Examples of the additive include antioxidants, ultraviolet light absorbents and plasticizers.

The organic EL device of the present invention can be used, for example, for a planar light emitting member for a flat panel display of wall televisions, a back light of copiers, printers and liquid crystal displays, a light source for instruments, a display panel and a marking light.

EXAMPLES

The present invention will be described more specifically with reference to Synthesis Examples and Examples in the following. However, the present invention is not limited to Synthesis Examples and Examples.

Synthesis Example 1 (Compound (B-1))

The routes of reactions for synthesizing intermediate compound b and intermediate compound d are shown in the following:

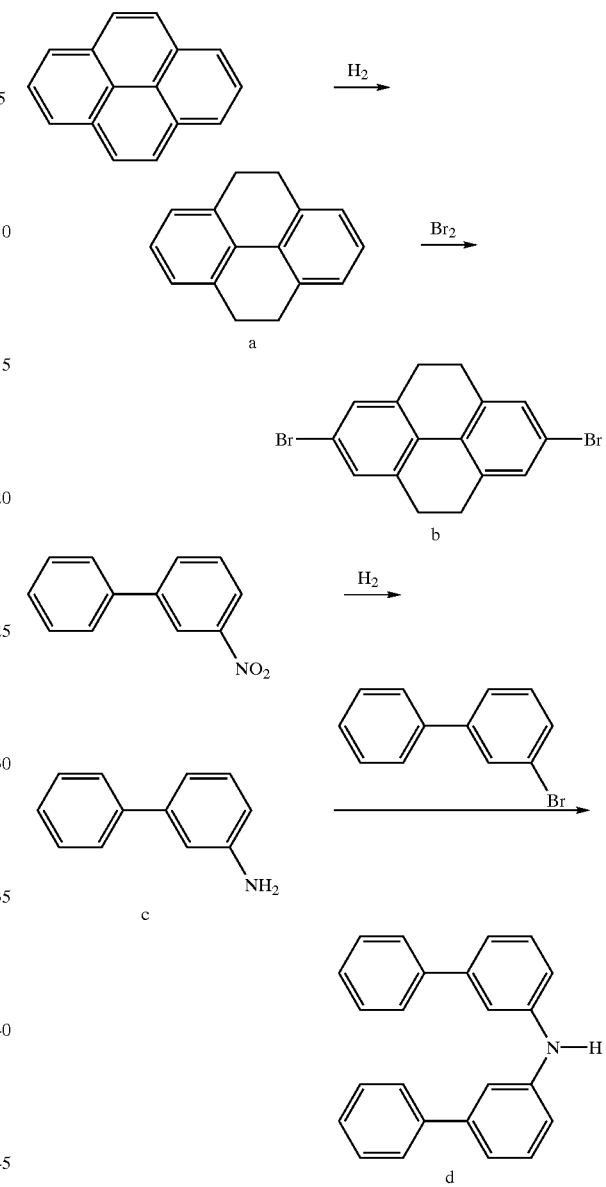

Synthesis of Intermediate Compound a

Into an autoclave, 19.5 g (96 mmole) of pyrene, 7.8 g of Pd/C (5%) and 100 ml of decaline were placed and the reaction was allowed to proceed under a hydrogen pressure of 70 kg/cm$^2$ at 160° C. for 2 hours. After the reaction as completed, the catalyst was removed and the remaining liquid was washed with 300 ml of chloroform. Then, chloroform was removed by distillation under a reduced pressure and the residual decaline solution was cooled with ice. The precipitated crystals were separated by filtration, washed with ethanol and dried by heating and 13 g (the yield: 64%) of intermediate compound a as the object compound was obtained.

Synthesis of Intermediate Compound b

Intermediate compound a in an amount of 12.6 g (60 mmole) was suspended in 1 liter of purified water and 0.2 g of FeCl$_3$.H$_2$O was added to the resultant suspension. Then, an aqueous solution obtained from 6.3 ml (2 equivalents) of bromine and 3 liters of purified water was added dropwise at the room temperature and the reaction was allowed to proceed at the same temperature for one night. After the reaction was completed, the precipitated crystals were separated by filtration, washed with water and ethanol and dried by heating and 3.2 g (the yield: 14%) of intermediate compound b as the object compound was obtained.

Synthesis of Intermediate Compound c

In a suspension containing 13 g (65 mmole) of 3-nitrodiphenyl in 75 ml of ethanol, 1 g of Pd/C (7.5%) was added and the reaction was allowed to proceed at a temperature of 30° C. or lower for 7 hours while hydrogen was blown into the reaction fluid. After the obtained reaction mixture was filtered and Pd/C was removed, the solvent was removed under a reduced pressure and 10.8 g (the yield: 98%) of intermediate compound c as the object compound was obtained.

Synthesis of Intermediate Compound d

Into a 300 ml three-necked flask equipped with a condenser, 6.8 g (40 mmole) of intermediate compound c, 9.2 g (40 mmole) of 3-bromophenyl, 1.1 g (1.5% by mole) of tris(dibenzylideneacetone)dipalladium, 0.72 g (3% by mole) of tri-o-tolylphosphine, 3.8 g (40 mmole) of sodium t-butoxide and 100 ml of dry toluene were placed and the resultant mixture was stirred under heating at 100° C. for one night. After the reaction was completed, the precipitated crystals were separated by filtration and washed with 100 ml of methanol and 11.8 g (the yield: 90%) of intermediate compound d was obtained.

Synthesis of Compound (B-1)

Into a 300 ml three-necked flask equipped with a condenser, 3.6 g (10 mmole) of intermediate compound b, 6.5 g (20 mmole) of intermediate compound d, 0.27 g (1.5% by mole) of tris(dibenzylideneacetone)dipalladium, 0.18 g (3% by mole) of tri-o-tolylphosphine, 2.9 g (30 mmole) of sodium t-butoxide and 100 ml of dry toluene were placed under argon and the resultant mixture was stirred under heating at 100° C. for one night. After the reaction was completed, the precipitated crystals were separated by filtration and washed with 100 ml of methanol and 5.0 g of a yellow powder was obtained. The obtained product was identified to be compound (B-1) by the measurements in accordance with NMR, IR and FD-MS (the field desorption mass spectroscopy) (the yield: 60%).

Synthesis Example 2 (Compound (B-2))

Synthesis of Intermediate Compound e

The route of the reaction for synthesizing intermediate compound e is shown in the following:

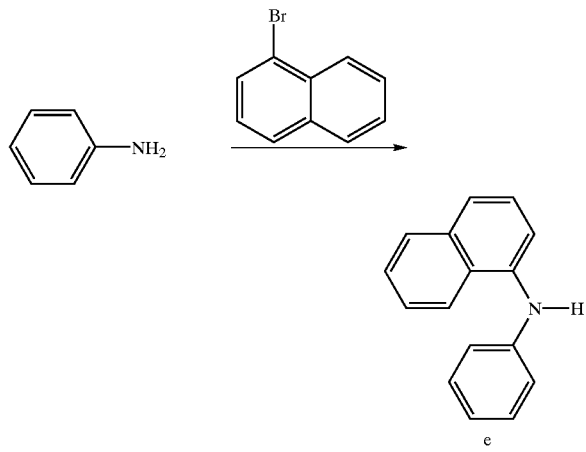

Into a 300 ml three-necked flask equipped with a condenser, 3.7 g (40 mmole) of aniline, 8.2 g (40 mmole) of 1-bromonaphthalene, 1.1 g (1.5% by mole) of tris (dibenzylideneacetone)dipalladium, 0.72 g (3% by mole) of tri-o-tolylphosphine, 3.8 g (40 mmole) of sodium t-butoxide and 100 ml of dry toluene were placed under argon and the resultant mixture was stirred under heating at 100° C. for one night. After the reaction was completed, the precipitated crystals were separated by filtration and washed with 100 ml of methanol and 8.3 g (the yield: 95%) of intermediate compound e was obtained.

Synthesis of Compound (B-2)

Into a 300 ml three-necked flask equipped with a condenser, 3.6 g (10 mmole) of intermediate compound b, 4.4 g (20 mmole) of intermediate compound e, 0.27 g (1.5% by mole) of tris(dibenzylideneacetone)dipalladium, 0.18 g (3% by mole) of tri-o-tolylphosphine, 1.9 g (20 mmole) of sodium t-butoxide and 100 ml of dry toluene were placed under argon and the resultant mixture was stirred under heating at 100° C. for one night. After the reaction was completed, the precipitated crystals were separated by filtration and washed with 100 ml of methanol and 4.5 g of a yellow powder was obtained. The obtained product was identified to be compound (B-2) by the measurements in accordance with NMR, IR and FD-MS (the yield: 70%).

Synthesis Example 3 (Compound (B-3))

Synthesis of Intermediate Compound f

The route of the reaction for synthesizing intermediate compound f is shown in the following:

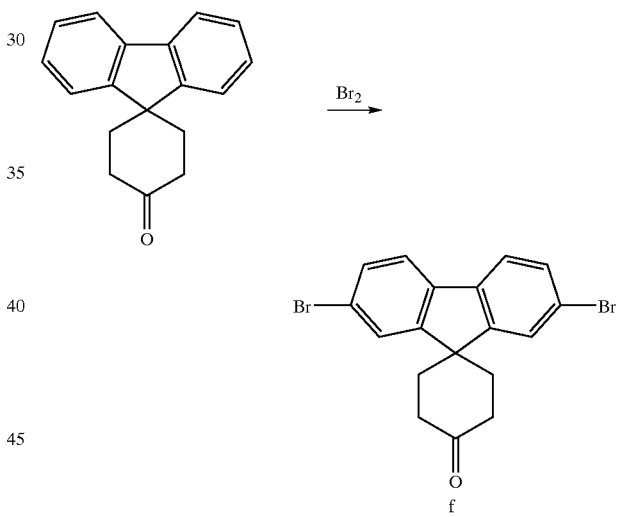

Into a 1 liter three-necked flask shielded from light, 12.4 g (50 mmole) of spiro[cyclohexane-1,9'-fluorene]-4-one (Journal of Organic Chemistry 26, 3280 (1961)), 100 ml of chloroform and 0.2 g of $FeCl_2$ were placed. Then, 24 g (0.15 mole) of bromine was added dropwise at 0° C. The reaction was allowed to proceed in the obtained mixture at the room temperature for one night. After the reaction was completed, the precipitated crystals were separated by filtration, washed with water and ethanol and dried by heating and 6.0 g (the yield: 30%) of intermediate compound f as the object compound was obtained.

Synthesis of Compound (B-3)

Into a 300 ml three-necked flask equipped with a condenser, 4.1 g (10 mmole) of intermediate compound f, 6.4 g (20 mmole) of intermediate compound d, 0.27 g (1.5% by mole) of tris(dibenzylideneacetone)dipalladium, 0.18 g (3% by mole) of tri-o-tolylphosphine, 1.9 g (20 mmole) of sodium t-butoxide and 100 ml of dry toluene were placed under argon and the resultant mixture was stirred under heating at 100° C. for one night. After the reaction was completed, the precipitated crystals were separated by filtration and washed with 100 ml of methanol and 4.4 g of a yellow powder was obtained. The obtained product was identified to be compound (B-3) by the measurements in accordance with NMR, IR and FD-MS (the yield: 50%).

Synthesis Example 4 (Compound (B-4))
Synthesis of Intermediate Compound g
The route of the reaction for synthesizing intermediate compound g is shown in the following:

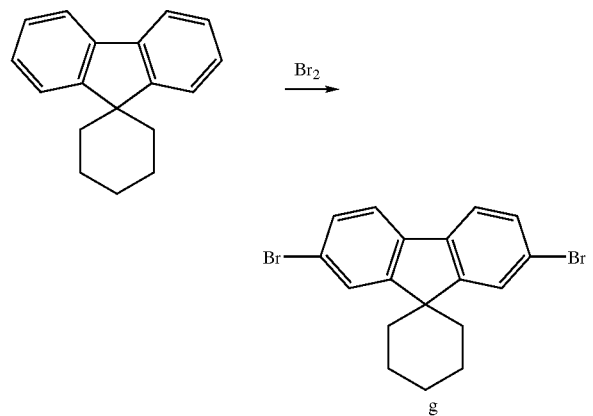

Into a 1 liter three-necked flask shielded from light, 11.7 g (50 mmole) of spiro[cyclohexane-1,9'-fluorene] (Journal of Organic Chemistry 26, 3280 (1961)), 100 ml of chloroform and 0.2 g of $FeCl_2$ were placed. Then, 24 g (0.15 mole) of bromine was added dropwise at 0° C. The reaction was allowed to proceed in the obtained mixture at the room temperature for one night. After the reaction was completed, the precipitated crystals were separated by filtration, washed with water and ethanol and dried by heating and 9.8 g (the yield: 50%) of intermediate compound g as the object compound was obtained.

Synthesis of Compound (B-4)
Into a 300 ml three-necked flask equipped with a condenser, 3.9 g (10 mmole) of intermediate compound g, 6.4 g (20 mmole) of intermediate compound d, 0.27 g (1.5% by mole) of tris(dibenzylideneacetone)dipalladium, 0.18 g (3% by mole) of tri-o-tolylphosphine, 1.9 g (20 mmole) of sodium t-butoxide and 100 ml of dry toluene were placed under argon and the resultant mixture was stirred under heating at 100° C. for one night. After the reaction was completed, the precipitated crystals were separated by filtration and washed with 100 ml of methanol and 6.1 g of a yellow powder was obtained. The obtained product was identified to be compound (B-4) by the measurements in accordance with NMR, IR and FD-MS (the yield: 70%).

Synthesis Example 5 (Compound (A-2))

The routes of the reactions for synthesizing intermediate compound h and intermediate compound i are shown in the following:

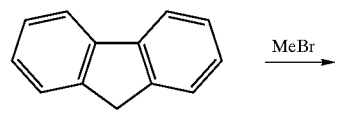

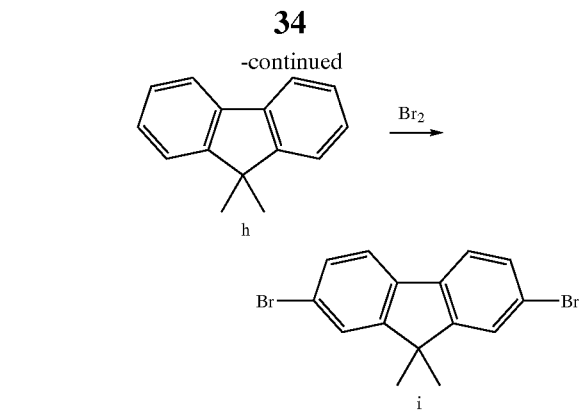

Synthesis of Intermediate Compound h
Into a 500 ml three-necked flask, 22 g (0.13 mmole) of fluorene and 100 ml of dry tetrahydrofuran were placed under argon and the resultant mixture was cooled at −78° C. To the cooled mixture, 120 ml of a hexane solution (2.6 M) of n-butyllithium (0.32 mole) was added dropwise. After the resultant solution was stirred at the same temperature for 1 hour, a solution prepared from 28 g (0.3 mole) of methyl bromide and 60 ml of tetrahydrofuran was added dropwise at −78° C. The temperature of the resultant solution was slowly raised to the room temperature and the solution was stirred for one night. After the reaction was completed, the reaction liquid was poured into 1 liter of water, subjected to extraction with isopropyl ether, washed with a saturated aqueous solution of sodium chloride and dried with anhydrous magnesium sulfate. The solvents were removed by distillation. The residue was purified by silica gel column chromatography (silica gel; the developing solvent: hexane) and 25 g (the yield: 98%) of intermediate compound h was obtained.

Synthesis of Intermediate Compound i
Into a 1 liter three-necked flask shielded from light, 9.7 g (50 mmole) of intermediate compound h, 100 ml of chloroform and 0.2 g of $FeCl_2$ were placed. Then, 24 g (0.15 mole) of bromine was added dropwise at 0° C. The reaction was allowed to proceed in the obtained mixture at the room temperature for one night. After the reaction was completed, the precipitated crystals were separated by filtration, washed with water and ethanol and dried by heating and 15 g (the yield: 85%) of intermediate compound i as the object compound was obtained.

Synthesis of Compound (A-2)
Into a 300 ml three-necked flask equipped with a condenser, 3.5 g (10 mmole) of intermediate compound i, 6.4 g (20 mmole) of intermediate compound d, 0.27 g (1.5% by mole) of tris(dibenzylideneacetone)dipalladium, 0.18 g (3% by mole) of tri-o-tolylphosphine, 1.9 g (20 mmole) of sodium t-butoxide and 100 ml of dry toluene were placed under argon and the resultant mixture was stirred under heating at 100° C. for one night. After the reaction was completed, the precipitated crystals were separated by filtration and washed with 100 ml of methanol and 6.6 g of a yellow powder was obtained. The obtained product was identified to be compound (A-2) by the measurements in accordance with NMR, IR and FD-MS (the yield: 80%).

Synthesis Example 6 (Compound (A-9))

The routes of the reactions for synthesizing intermediate compound j, intermediate compound k and intermediate compound M are shown in the following:

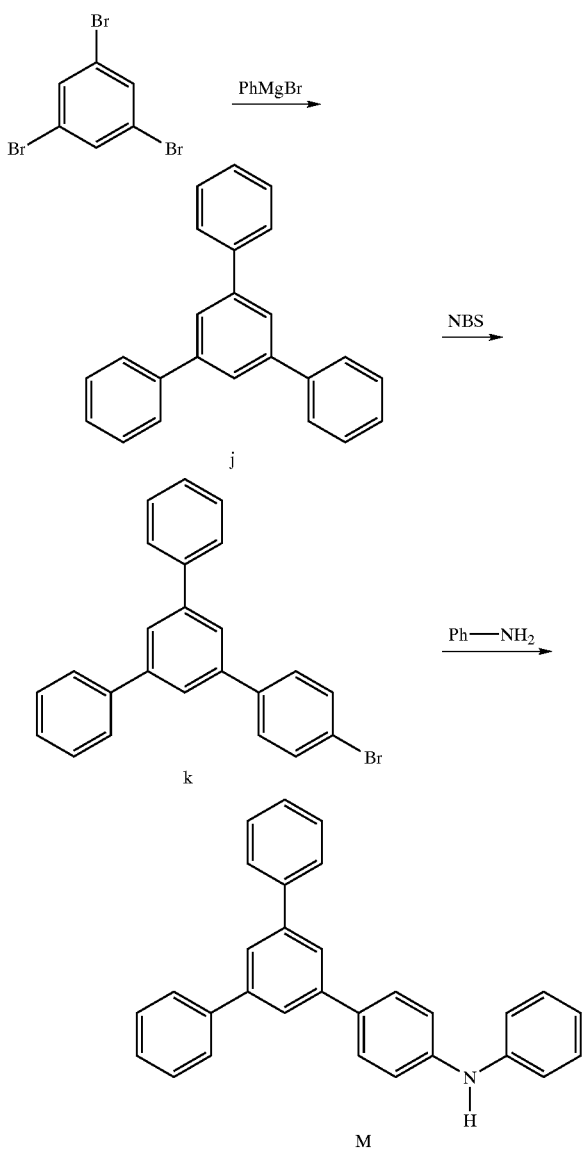

Synthesis of Intermediate Compound j

Into a 1 liter three-necked flask, 31 g (0.1 mmole) of 1,3,5-tribromobenzene, 4 g (5% by mole) of dichlorobis(triphenylphosphine)palladium, 10 ml (1 mmole) of a toluene solution (1.0 M) of diisobutylaluminum and 200 ml of tetrahydrofuran were placed under argon. To the resultant solution, 250 ml of a tetrahydrofuran solution (2.0 M) of phenylmagnesium bromide prepared in accordance with a conventional process was added dropwise at the room temperature. The temperature of the obtained solution was raised and the solution was refluxed for one night. After the reaction was completed, the reaction liquid was cooled with ice water. The precipitated crystals were separated by filtration, washed with 100 ml of methanol and 50 ml of acetone, successively, and 15.6 g (the yield: 51%) of intermediate compound j was obtained.

Synthesis of Intermediate Compound k

Into a 500 ml three-necked flask, 15.3 g (50 mmole) of intermediate compound j, 9 g (50 mmole) of N-bromosuccinimide, 0.41 g (5% by mole) of 2,2'-azoisobutyronitrile and 200 ml of dimethylformamide were placed under argon and the resultant solution was stirred at 110° C. for 4 hours. After the reaction was completed, insoluble substances were removed by filtration and the filtrate was concentrated under a reduced pressure using a rotary evaporator. The obtained crude crystals were purified by silica gel column chromatograpy and 11.5 g (the yield: 60%) of intermediate compound k was obtained.

Synthesis of Intermediate Compound M

Into a 300 ml three-necked flask equipped with a condenser, 11.5 g (30 mmole) of intermediate compound k, 9.3 g (0.1 mole) of aniline, 0.8 g (1.5% by mole) of tris(dibenzylideneacetone)dipalladium, 0.54 g (3% by mole) of tri-o-tolylphosphine, 5.7 g (60 mmole) of sodium t-butoxide and 100 ml of dry toluene were placed under argon and the resultant mixture was stirred under heating at 100° C. for one night. After the reaction was completed, the precipitated crystals were separated and washed with 100 ml of methanol and 10.7 g (the yield: 90%) of intermediate compound M was obtained.

Synthesis of Compound (A-9)

Into a 300 ml three-necked flask equipped with a condenser, 3.5 g (10 mmole) of intermediate compound i, 8.0 g (20 mmole) of intermediate compound M, 0.27 g (1.5% by mole) of tris(dibenzylideneacetone)dipalladium, 0.18 g (3% by mole) of tri-o-tolylphosphine, 1.9 g (20 mmole) of sodium t-butoxide and 100 ml of dry toluene were placed under argon and the resultant mixture was stirred under heating at 100° C. for one night. After the reaction was completed, the precipitated crystals were separated by filtration and washed with 100 ml of methanol and 4.9 g of a yellow powder was obtained. The obtained product was identified to be compound (A-9) by the measurements in accordance with NMR, IR and FD-MS (the yield: 50%).

Example 1

A glass substrate (manufactured by GEOMATEC Company) of 25 mm×75 mm×1.1 mm thickness having an ITO transparent electrode was cleaned by application of ultrasonic wave in isopropyl alcohol for 5 minutes and then by exposure to ozone generated by ultraviolet light for 30 minutes. The glass substrate having the transparent electrode lines which had been cleaned was attached to a substrate holder of a vacuum vapor deposition apparatus. On the surface of the cleaned substrate at the side having the transparent electrode, a film of N,N'-bis(N,N'-diphenyl-4-aminophenyl)-N,N'-diephenyl-4,4'-diamino-1,1'-biphenyl (referred to as TPD232, hereinafter) having a thickness of 60 nm was formed in a manner such that the formed film covered the transparent electrode. The formed film of TPD232 worked as the hole injecting layer. Then, on the formed film of TPD232, a film of the above hole transporting compound (compound (A-2)) having a thickness of 20 nm was formed. The formed film of compound (A-2) worked as the hole transporting layer. On the formed film of compound (A-2), a film of tris(8-quinolinol)aluminum (referred to as Alq, hereinafter) having a thickness of 40 nm was formed. The film of Alq worked as the light emitting layer. Thereafter, Li (the source of lithium: manufactured by SAES GETTERS Company) and Alq were binary vapor deposited and an Alq:Li film having a thickness of 20 nm was formed as the electron injecting layer (the cathode). On the formed Alq:Li film, metallic aluminum was vapor deposited to form a metal cathode and an organic El device was prepared.

When a direct current voltage of 6 V was applied to the organic EL device prepared above, blue light was emitted at a luminance of 153 cd/m$^2$, the maximum luminance of 50,000 cd/m$^2$ and an efficiency of light emission of 3.2 cd/A.

As the test of storage under heating, the organic EL device was kept in the environment of 100° C. for 500 hours. After the test, a direct current voltage of 6 V was applied to the organic EL device. A luminance which was 98% of the original luminance was obtained and the percentage of residual luminance was 98%.

Examples 2 to 7

Organic EL devices were prepared in accordance with the same procedures as those conducted in Example 1 except that the compounds shown in Table 1 were used in place of compound (A-2) used in Example 1. The luminance of light emission and the efficiency of light emission were measured and the color of the emitted light was observed under application of a direct current voltage of 6 V. As the test of storage under heating, the organic EL device was kept in the environment of 85° C. for 500 hours. After the test, the percentage of residual luminance based on the original luminance was measured. The results are shown in Table 1.

Comparative Example 1

An organic EL device was prepared in accordance with the same procedures as those conducted in Example 1 except that compound (A-2) used in Example 1 was replaced with the following compound TPAF (glass transition temperature: lower than 100° C.):

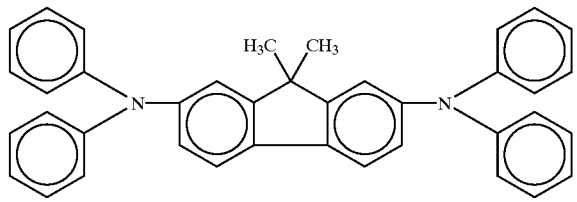

The luminance of light emission and the efficiency of light emission were measured and the color of the emitted light was observed under application of a direct current voltage of 5 V. As the test of storage under heating, the organic EL device was kept in the environment of 85° C. for 500 hours. After the test, the percentage of residual luminance based on the original luminance was measured. The results are shown in Table 1.

transition temperatures as high as 100° C. or higher and the interaction with the light emitting layer was absent.

Example 8

A glass substrate (manufactured by GEOMATEC Company) of 25 mm×75 mm×1.1 mm thickness having an ITO transparent electrode was cleaned by application of ultrasonic wave in isopropyl alcohol for 5 minutes and then by exposure to ozone generated by ultraviolet light for 30 minutes. The glass substrate having the transparent electrode lines which had been cleaned was attached to a substrate holder of a vacuum vapor deposition apparatus. On the surface of the cleaned substrate at the side having the transparent electrode, a film of TPD232 having a thickness of 60 nm was formed in a manner such that the formed film covered the transparent electrode. The formed film of TPD232 worked as the hole injecting layer. Then, on the formed film of TPD232, a film of the above hole transporting compound (compound (B-4)) having a thickness of 20 nm was formed. The formed film of compound (B-4) worked as the hole transporting layer. On the formed film of compound (B-4), Alq and rubrene were binary vapor deposited so that a film having a thickness of 40 nm and containing Alq and rubrene in relative amounts by weight of 30:1 was formed. The film of Alq and rubrene worked as the light emitting layer. On the film of Alq and rubrene thus formed, a film of Alq having a thickness of 20 nm was formed. The formed film of Alq worked as the electron injecting layer. Thereafter, Li (the source of lithium: manufactured by SAES GETTERS Company) and Alq were binary vapor deposited and an Alq:Li film was formed as the electron injecting layer (the cathode). On the formed Alq:Li film, metallic aluminum was vapor deposited to form a metal cathode and an organic El device was prepared.

When a direct current voltage of 6 V was applied to the organic EL device prepared above, yellow light was emitted at a luminance of 250 cd/m$^2$, the maximum luminance of 98,000 cd/m$^2$ and an efficiency of light emission as high as 9.5 cd/A. The half-life of the organic EL device was as long as 6,900 hours in the life test in which the device was driven under a constant current at an initial luminance of 1,000 cd/m$^2$.

As shown above, the novel arylamine compound of the present invention was very excellent as the hole transporting compound.

TABLE 1

| | Compound | Voltage (V) | Luminance of emitted light (cd/m$^2$) | Efficiency of light emission (cd/A) | Color of emitted light | Percentage of residual luminance (%) |
|---|---|---|---|---|---|---|
| Example 2 | (B-1) | 6 | 130 | 3.5 | green | 98 |
| Example 3 | (B-2) | 6 | 131 | 3.7 | green | 96 |
| Example 4 | (B-3) | 6 | 155 | 3.7 | green | 99 |
| Example 5 | (B-4) | 6 | 310 | 3.8 | green | 105 |
| Example 6 | (A-2) | 6 | 320 | 4.1 | green | 101 |
| Example 7 | (A-9) | 6 | 260 | 4.0 | green | 96 |
| Comparative Example 1 | TPAF | 5 | 150 | 2.5 | green | 56 |

As shown in Table 1, the organic EL devices of the present invention which were obtained by using the novel arylamine compounds exhibited high luminances and high efficiencies of light emission and had excellent heat resistance. These advantageous results could be obtained since the novel arylamine compounds of the present invention had glass Comparative Example 2

An organic EL device was prepared in accordance with the same procedures as those conducted in Example 8 except that the above compound TPAF was used in place of the above compound (B-4).

The half-life of the organic EL device prepared above was as short as 750 hours in the life test in which the device was driven under a constant current at an initial luminance of 1,000 cd/m$^2$.

INDUSTRIAL APPLICABILITY

As described in detail in the above, the organic EL devices utilizing the novel arylamine compound of the present invention had the high luminance, the high heat resistance, the long life and the excellent hole transporting property and emits light at the high efficiency.

Therefore, the organic EL device of the present invention is advantageously used for the light source such as the planar light emitting member for wall televisions and the back light of displays.

What is claimed is:

1. A novel arylamine compound represented by the following general formula (1):

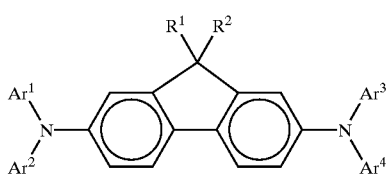

(1)

wherein R$^1$ and R$^2$ each independently represent a substituted or unsubstituted alkyl group having 1 to 30 carbon atoms, a substituted or unsubstituted alkoxyl group having 1 to 30 carbon atoms, a substituted or unsubstituted aryl group having 6 to 40 carbon atoms, a substituted or unsubstituted arylalkyl group having 7 to 40 carbon atoms or a substituted or unsubstituted aryloxyl group having 6 to 40 carbon atom; and Ar$^1$ to Ar$^4$ each independently represent a substituted or unsubstituted aryl group having 6 to 40 carbon atoms or a substituted or unsubstituted heterocyclic group having 5 to 40 carbon atoms and may represent a same group or different groups, with provisos that at least two of Ar$^1$ to Ar$^4$ each represent a substituted or unsubstituted m-biphenyl group or biphenyl group substituted with aryl groups and others of Ar$^1$ to Ar$^4$ each represent a substituted or unsubstituted biphenyl group and that, when at least two of Ar$^1$ to Ar$^4$ each represent biphenyl group substituted with two aryl groups, others of Ar$^1$ to Ar$^4$ each represent a substituted or unsubstituted aryl group.

2. A novel arylamine compound according to claim 1, wherein, in general formula (1), Ar$^1$ and Ar$^3$ each represent a substituted or unsubstituted m-biphenyl group and Ar$^2$ and Ar$^4$ each represent a substituted or unsubstituted biphenyl group.

3. An electroluminescence device comprising a pair of electrodes and a layer of organic compounds disposed between the pair of electrodes, wherein the layer of organic compounds comprises a novel arylamine compound described in claim 1.

4. An organic electroluminescence device according to claim 3, wherein the layer of organic compounds is a light emitting layer or a hole transporting layer.

5. An organic electroluminescence device comprising a pair of electrodes and a layer of organic compounds disposed between the pair of electrodes, wherein the layer of organic compounds comprises a layer comprising a novel arylamine compound described in claim 1 and a light emitting material.

* * * * *